(12) United States Patent
Tse et al.

(10) Patent No.: US 11,964,281 B2
(45) Date of Patent: Apr. 23, 2024

(54) SYSTEM AND METHOD FOR CORRECTING PATIENT INDEX

(71) Applicant: CytoVale Inc., San Francisco, CA (US)

(72) Inventors: Henry Tat Kwong Tse, San Francisco, CA (US); Ajay M. Shah, San Francisco, CA (US); Lionel Guillou, San Francisco, CA (US); Roya Sheybani, San Francisco, CA (US); Audun Johnson, San Francisco, CA (US); Peter Landwehr, San Francisco, CA (US); Hunter Stevenson, San Francisco, CA (US)

(73) Assignee: CytoVale Inc., San Francisco, CA (US)

( * ) Notice: Subject to any disclaimer, the term of this patent is extended or adjusted under 35 U.S.C. 154(b) by 0 days.

(21) Appl. No.: 17/592,040

(22) Filed: Feb. 3, 2022

(65) Prior Publication Data
US 2023/0241612 A1 Aug. 3, 2023

(51) Int. Cl.
B01L 3/00 (2006.01)
G01N 33/50 (2006.01)
G06T 7/00 (2017.01)

(52) U.S. Cl.
CPC ... B01L 3/502761 (2013.01); B01L 3/502715 (2013.01); G01N 33/5094 (2013.01); G06T 7/0012 (2013.01); B01L 2200/0663 (2013.01); B01L 2300/0654 (2013.01); G06T 2207/30024 (2013.01)

(58) Field of Classification Search
CPC ..... B01L 2200/0663; B01L 2300/0654; B01L 2300/0877; B01L 3/502715; B01L 3/502753; B01L 3/502761; G06T 2207/10056; G06T 2207/30024; G06T 2207/30242; G06T 7/0012; G01N 33/5094

See application file for complete search history.

(56) References Cited

U.S. PATENT DOCUMENTS

| 4,654,312 A | 3/1987 | Chang et al. |
| 4,902,613 A | 2/1990 | Chang et al. |
| 5,155,044 A | 10/1992 | Ledis et al. |
| 5,798,827 A | 8/1998 | Frank et al. |
| 8,935,098 B2 | 1/2015 | Di Carlo et al. |

(Continued)

FOREIGN PATENT DOCUMENTS

| EP | 2619545 B1 | 1/2019 |
| JP | 2001211896 A | 8/2001 |

(Continued)

OTHER PUBLICATIONS

"BD FACS Lyse Wash Assistant Streamline Sample Preparation Workflow", BD Biosciences, For In Vitro Diagnostics Use, 2010.

(Continued)

Primary Examiner — Dean Kwak
(74) Attorney, Agent, or Firm — Jeffrey Schox; Randy Mehlenbacher

(57) ABSTRACT

A system and/or method for determining an immune activation state of a subject can include: deforming leukocytes within a microfluidic channel, acquiring a plurality of images of the leukocytes, determining biophysical parameters of the leukocyte, adjusting the biophysical parameters, and determining the immune activation state of the subject based on the biophysical parameters.

13 Claims, 5 Drawing Sheets

(56) References Cited

U.S. PATENT DOCUMENTS

| | | | |
|---|---|---|---|
| 9,151,705 | B2 | 10/2015 | Di Carlo et al. |
| 9,414,990 | B2 | 8/2016 | Ivosevic et al. |
| 9,464,977 | B2 | 10/2016 | Di Carlo et al. |
| 9,638,620 | B2 | 5/2017 | Di Carlo et al. |
| 9,897,532 | B2 | 2/2018 | Di Carlo et al. |
| 10,107,735 | B2 | 10/2018 | Di Carlo et al. |
| 10,808,219 | B2 | 10/2020 | Masaeli et al. |
| 11,521,706 | B2 | 12/2022 | Xin et al. |
| 11,548,003 | B1 | 1/2023 | Tse et al. |
| 2005/0070005 | A1 | 3/2005 | Keller |
| 2005/0221396 | A1 | 10/2005 | Simon-Lopez |
| 2006/0139638 | A1 | 6/2006 | Muller et al. |
| 2006/0210438 | A1 | 9/2006 | Nagai et al. |
| 2008/0077072 | A1 | 3/2008 | Keenan et al. |
| 2009/0014360 | A1 | 1/2009 | Toner et al. |
| 2013/0177935 | A1 | 7/2013 | Di et al. |
| 2013/0224851 | A1 | 8/2013 | Ljungmann et al. |
| 2014/0087412 | A1 | 3/2014 | Fouras et al. |
| 2014/0113324 | A1 | 4/2014 | Di Carlo et al. |
| 2014/0227777 | A1 | 8/2014 | Choi et al. |
| 2014/0315287 | A1 | 10/2014 | Di Carlo et al. |
| 2015/0355073 | A1 | 12/2015 | Di Carlo et al. |
| 2016/0231224 | A1 | 8/2016 | Di Carlo et al. |
| 2017/0089822 | A1 | 3/2017 | Di Carlo et al. |
| 2017/0234788 | A1 | 8/2017 | Di Carlo et al. |
| 2017/0284924 | A1* | 10/2017 | Tse ................ B01L 3/00 |
| 2018/0128735 | A1 | 5/2018 | Di Carlo et al. |
| 2018/0267021 | A1 | 9/2018 | Suresh et al. |
| 2018/0305758 | A1 | 10/2018 | Shi et al. |
| 2019/0092757 | A1 | 3/2019 | Ashford et al. |
| 2019/0143326 | A1 | 5/2019 | Irimia et al. |
| 2021/0031198 | A1* | 2/2021 | Tse Kwong ........... G16H 30/40 |
| 2021/0110545 | A1 | 4/2021 | Herold et al. |
| 2021/0181086 | A1 | 6/2021 | Chou et al. |

FOREIGN PATENT DOCUMENTS

| | | | | |
|---|---|---|---|---|
| JP | 2009511998 | A | 3/2009 | |
| KR | 100889617 | B1 | 3/2009 | |
| KR | 100889618 | B1 | 3/2009 | |
| KR | 100965222 | B1 | 6/2010 | |
| WO | 2004113908 | A1 | 12/2004 | |
| WO | 2007047761 | A1 | 4/2007 | |
| WO | 2009069418 | A1 | 6/2009 | |
| WO | 2012040067 | A2 | 3/2012 | |
| WO | 2014113110 | A2 | 7/2014 | |
| WO | 2018213721 | A1 | 11/2018 | |
| WO | WO-2020011487 | A1 * | 1/2020 | ......... G01N 15/1475 |
| WO | 2021022050 | A1 | 2/2021 | |

OTHER PUBLICATIONS

"BD FACS™ Lyse Wash Assistant", BD Biosciences, https://www.bdbiosciences.com/en-us/products/instruments/sample-prep-systems/facs-lyse-wash-assistant.

"Cytovale", https://cytovale.com.

"TQ-Prep Workstation", Beckman Coulter Lifesciences, https://www.beckman.com/flow-cytometry/instruments/tq-prep.

Bhagat, Ali Asgar, et al., "Intertial microfluidics for sheath-less high-throughput cytometry", Biomed. Microdevices 12(2), 187-195 (2010).

Bow, Hansen, et al., "A microfabricated deformability-based flow cylometer with application to malaria", Lab Chip. Mar. 21, 2011; 11(6): 1065-1073. doi:10.1039/c0lc00472c.

Cha, Sukgyen, et al., "Cell Stretching Measurement Utilizing Viscoelastic Particle Focusing", Anal. Chem., 2012, 84, 10471-10477.

Chambers, Ann F., et al., "Metastasis: dissemination and growth of cancer cells in metastatic site", Nature Reviews cancer, vol. 2(8), p. 563-572, 2002.

Chen, J., et al., "Classification of cell types using a microfluidic device for mechanical and electrical measurement on single cells", Lab Chip, 2011, 11, 3174-3181., Oct. 31, 2017 00:00:00.0.

Choi, Sungyoung, et al., "Sheathless hydrophoretic particle focusing in a microchannel with exponentially increasing obstacle arrays", Anal Chem., 80(8):3035-9 (2008)., Oct. 31, 2017 00:00:00.0.

Crawford, Katherine, et al., "Rapid Biophysical Analysis of Host Immune Cell Variations Associated with Sepsis", American Journal of Respiratory and Critical Care Medicine, vol. 198, No. 2, Jul. 15, 2018.

Cross, Sarah E., et al., "Nanomechanical analysis of cells from cancer patients", Nat Nano 2:780-783 (2007)., Oct. 31, 2017 00:00:00.0.

Di Carlo, Dino, et al., "Continuous inertial focusing, ordering, and separation of particles in microchannels", Proc Natl Acad Sci USA 104:18892-18897 (2007).

Di Carlo, Dino, et al., "Dynamic Single-Cell Analysis for Quantitative Biology", Analytical Chemistry 78:7918-7925 2006.

Di Carlo, Dino, et al., "Inertial microfluidics", Lab Chip 9:3038-3046 (2009)., Oct. 31, 2017 00:00:00.0.

Di Carlo, Dino, et al., "Particle Segregation and Dynamics in Confined Flows", Phys. Rev. Lett. 102 (2009)., Oct. 31, 2017 00:00:00.0.

Dobbe, J.G.G., et al., "Measurement of the Distribution of Red Blood Cell Deformability Using an Automated Rheoscope", Cytometry (Clinical Cytometry), vol. 50, pp. 313-325, 2002., Oct. 31, 2017 00:00:00.0.

Dudani, Jaideep S., et al., "Pinched-flow hydrodynamic stretching of single-cells+", Lab Chip, 2013, 13, 3728., Oct. 31, 2017 00:00:00.0.

Dylla-Spears, Rebecca, et al., "Single-molecule detection via microfluidic planar extensional flow at a stagnation point", Lab on a Chip, vol. 10, pp. 1543-1549, Mar. 2010., Oct. 31, 2017 00:00:00.0.

Fardi, Muhammad Asim, et al., "Elasto-inertial microfluidics for bacteria separation from whole bloods for sepsis diagnostics", Journal of Nanobiotechnology, (2017) 15:3.

Fregin, Bob, et al., "High-throughput single-cell rheology in complex samples by dynamic real-time deformability cytometry", Nature Communications, (2019)10:415.

Gossett, D.R., et al., "Deformability Cytometry: High-Throughput, Continuous Measurement of Cell Mechanical Properties in Extensional Flow", 14th International Conference on Miniaturized Systems for Chemistry and Life Sciences Oct. 3-7, 2010, Groningen, The Netherlands.

Gossett, Daniel R, et al., "Hydrodynamic stretching of single cells for large population mechanical phenotyping", 7630-7635, PNAS, May 15, 2012, vol. 1091, No. 20.

Gossett, Daniel R., et al., "Label-free cell separation and sorting in microfluidic systems", Apr. 25, 2010, Springer, Anal. Bioanal. Chem., 397, pp. 3249-3267.

Gossett, Daniel R., et al., "Leukocyte Mechanophenotyping by Deformability Cytometry", 16th International Conference on Miniaturized Systems for Chemistry and Life Sciences Oct. 28-Nov. 1, 2012, Okinawa, Japan (3 pages).

Gossett, Daniel R., et al., "Particle focusing mechanisms in curving confined flows", Anal Chem 81:8459-8465 (2009)., Oct. 31, 2017 00:00:00.0.

Guck, J., et al., "Optical Deformability as an Inherent Cell Marker for Testing Malignant Transformation and Metastatic Competence", Biophysical Journal, vol. 88, May 2005, 3689-3698.

Guillou, Lionel, et al., "Development and validation of a cellular host response test as an early diagnostic for sepsis", PLOS One, Research Article, Apr. 15, 2021.

Gunsolus, Ian L., et al., "Diagnosing and Managing Sepsis by Probing the Host Response to Infection: Advances, Opportunities, and Challenges", Journal of Clinical Microbiology, vol. 57, Issue 7, Jul. 2019.

Guo, Q., "Microfluidic Device for Measuring the Deformability of Single Cells", Doctorate Thesis, The University of British Columbia, Apr. 2012, 1-24 (total 78 pages., Oct. 31, 2017 00:00:00.0.

Lee, Won Hee, et al., "Dynamic self-assembly and control of microfluidic particle crystals", Proc. Natl. Acad. Sci. U.S.A, 107, 22413-22418 (2010).

(56) References Cited

OTHER PUBLICATIONS

Lincoln, Bryan, et al., "Deformability-Based Flow Cytometry", Cytometry Part A, vol. 59A, pp. 203-209, 2004., Oct. 31, 2017 00:00:00.0.

Mao, Xiaole, et al., "Single-layer planar on-chip flow cytometer using microfluidic drifting based three-dimensional (3D) hydrodynamic focusing", Lab Chip, 9, 1583-1589 (2009).

Morton, K.J., et al., "Crossing microfluidic streamlines to lyse, label and wash cells", Lab Chip 8, 1448-1453 (2008).

Mutlu, Baris R., et al., "Oscillatory inertial focusing in infinite microchannels", PNAS, vol. 115, No. 30, 7682-7687, Jul. 24, 2018.

Natu, Rucha, et al., "Assessment of Flow through Microchannels for Inertia-Based Sorting: Steps toward Microfluidic Medical Devices", Micromachines, 2020, 11, 886, publishedSep. 24, 2020.

Oakey, John, et al., "Particle Focusing in Staged Inertial Microfluidic Devices for Flow Cytometry", Anal. Chem., 82, 3862-3867 (2010).

Oeschger, Taylor, et al., "Point of care technologies for sepsis diagnosis and treatment", Lab Chip, 2019, 19, 728-737.

Park, Jae-Sung, et al., "Continuous focusing of microparticles using intertial lift force and vorticity via multi-orifice microfluidic channels", Lab on a Chip, 9, 939-48 (2009)., Oct. 31, 2017 00:00:00.0.

Perkins, Thomas T., et al., "Single Polymer Dynamics in an Elongational Flow", Science 276:2016-2021 (1997)., Oct. 31, 2017 00:00:00.0.

Petersson, F., et al., "Carrier Medium Exchange through Ultrasonic Particle Switching in Microfluidic Channels", Anal. Chem. 77, 1216-1221 (2005).

Sawetzki, Tobias, et al., "Viscoelasticity as a Biomarker for High-Throughput Flow Cytometry", Biophysical Journal, vol. 105, Nov. 2013, pp. 2281-2288.

Shelby, Patrick J., et al., "A microfluidic model for single-cell capillary obstruction by Plasmodium falciparum-infected erythrocytes", PNAS, vol. 100, pp. 14618-14622, 2003., Oct. 31, 2017 00:00:00.0.

Squires, Todd M., et al., "Microfluidics: Fluid physics at the nanoliter scale", Rev. of Modern Physics, vol. 77, pp. 977-1026, 2005.

Sraj, Ihab, et al., "Cell deformation cytometry using diode-bar optical stretchers", J Biomed Opt 15 (2010)., Oct. 31, 2017 00:00:00.0.

Suresh, S., et al., "Connections between single-cell biomechanics and human disease states: gastrointestinal cancer and malaria", Acta Biomater 1:15-30 (2005)., Oct. 31, 2017 00:00:00.0.

Thery, Manuel, et al., "Get round and stiff for mitosis", HFSP J 2:65-71 (2008)., Oct. 31, 2017 00:00:00.0.

Tornay, R., et al., "Dielectrophoresis-based particle exchanger for the manipulation and surface functionalization of particles", Lab Chip 8, 267-273 (2008).

Tse, Henry T.K., et al., "Quantitative Diagnosis of Malignant Pleural Effusions by Single-Cell Mechanophenotyping", Science Translational Medicine, Nov. 20, 2013: vol. 5, Issue 212, pp. 212ra163.

Yamada, Masumi, et al., "Hydrodynamic filtration for on-chip particle concentration and classification utilizing microfluidics", Lab Chip, 5, 1233-1239 (2005)., Oct. 31, 2017 00:00:00.0.

Yamada, M., et al., "Millisecond treatment of cells using microfluidic devices via two-step carrier medium exchange", Lab Chip, 8, 772-778 (2008).

Yap, Belinda, et al., "Cystoskeletal remodeling and cellular activation during deformation of neutrophils into narrow channels", J. Appl. Physiol, vol. 99, pp. 2323-2330, 2005., Oct. 31, 2017 00:00:00.0.

Young, Susan M., et al., "High-Throughput Microfluidic Mixing and Multiparametric Cell Sorting for Bioactive Compound Screening", J. Biomol Scree, vol. 9, pp. 103-111, 2004., Oct. 31, 2017 00:00:00.0.

Zhang, Xunil, et al., "Continuous flow separation of particles within an asymmetric microfluidic device", 2006, RSC, :ab Chip, 6, 561-566.

Zhang, J., et al., "Inertial focusing in a straight channel with asymmetrical expansion-contraction cavity arrays using two secondary flows", J. Micromech. Microeng. 23 (2013) 08023 (13pp).

Zheng, Bo, "Formation of Droplets of Alternating Composition in Microfluidic Channels and Applications to Indexing of Concentrations in Droplet-Based Assays", Anal. Chem., vol. 76, pp. 4977-4982, 2004., Oct. 31, 2017 00:00:00.0.

Minamitani, Haruyuki, et al., "Deformability Cytometry: High-Throughput, Continuous Measurement of Cell Mechanical Properties in Extensional Flow", BMES/EMBS Conference, 1999, Proceedings of the First Joint Atlanta, GA, USA Oct. 13-16, 1999, Piscataway, NJ, USA, IEEE, US, vol. 1, Oct. 13, 1999 Oct. 13, 1999_, p. 72, XPO10357477, DoI: 10.1109/IEMBS. 1999.802107, ISBN: 978-0-7803-5674-0.

Rosenbluth, Michael J, "Analyzing cell mechanics in hematologic diseases with microfluidic biophysical flow cytometry", Lab on a Chip 8.7 (2008): 1062-1070. (Year: 2008.

Issekutz, Andrew C., "Role of ICAM-1 and ICAM-2 and alternate CD11/CD18 ligands in neutrophil transendothelial migration", 1999, 65, 117-126 (Year 199).

Jalali, Bahram, et al., "Evolution of Photonic Time Stretch: From Analog to Digital Conversion to Blood Screening", arXiv:1106.5518 physics.ins-det, Submitted Jun. 27, 2011.

Ellet Felix, "Diagnosis of sepsis from a drop of blood by measurement of spontaneous neutrophil motility in a microfluidic assay", Nature biomedical engineering 2.4 (2018): 207-214. (Year: 2018).

\* cited by examiner

Receive a dataset associated with leukocytes of a patient S100

Filter the dataset S200

Determine metric from the dataset S300

Adjust the metric S400

Determine health state of the patient S500

Provision an intervention based on the health state S600

Filter out event

Filter out event

US 11,964,281 B2

SYSTEM AND METHOD FOR CORRECTING PATIENT INDEX

TECHNICAL FIELD

This invention relates generally to the health field, and more specifically to a new and useful system and method in the health field.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figures 1, 2:
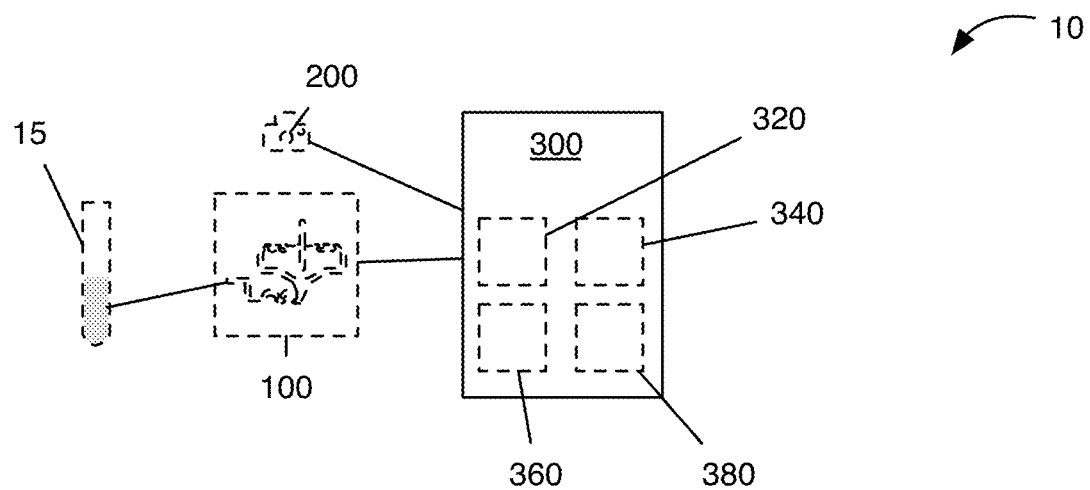
FIG. 1 is a schematic representation of the apparatus.
FIG. 2 is a schematic representation of the method.
Figure 3:
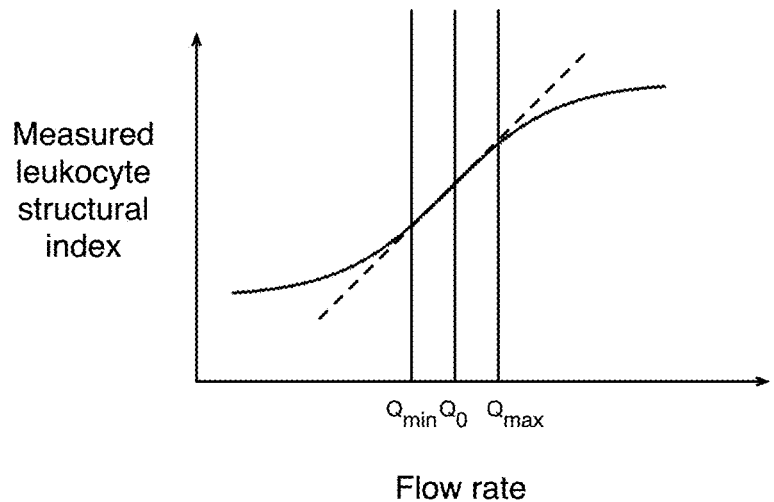
FIG. 3 is a schematic representation of an example of a flow rate range over which an adjustment is applied.

As shown in FIG. 1, the system 10 can include an image acquisition system 200, a sample cartridge 100, a computing system 300, and/or any suitable components. The computing system 300 can include an image analyzer 320, filter 340, adjuster 360, index calculator, health scorer 380, and/or any suitable components or modules.

As shown in FIG. 2, the method 20 can include receiving a dataset associated with a patient S100, filtering the dataset S200, determining a metric from the dataset S300, adjusting the metric S400, determining an immune activation state of the patient S500, provisioning an intervention to the patient S600, and/or any suitable steps.

The system and method are preferably used to measure and detect biophysical properties of cells, but can measure properties of any particle and/or material (e.g., that fits in the microfluidic channels). The system and/or method can additionally or alternatively function to diagnose a health state (e.g., an immune activation state of) of a subject (e.g., patient). In a specific example, the system and/or method can be used in an emergency department (e.g., of a hospital), urgent care, and/or doctor's office to triage patients (e.g., diagnoses and/or determined probability that a patient is experiencing a condition such as a sepsis-related condition). However, the system and/or method can be used in any manner.

2. Benefits

Variations of the technology can confer several benefits and/or advantages.

First, variants of the technology can improve a reproducibility, repeatability, and/or a reliability of a patient sample analysis. The enhanced reproducibility, repeatability, and/or reliability can be across different practitioners, different medical practices, different geographical areas, different times (e.g., hours, days, weeks, months, years, etc.), different systems, and/or in any suitable conditions. For instance, the system and/or method can achieve a reproducibility of 1.0 score units (e.g., where the score can range from about 0 to 10, 0 to 100, and/or have any suitable range), where the score can be associated with an immune activation state. In another illustrative example, the system and/or method can achieve a reproducibility of at least 10% (e.g., 0.01%, 0.05%, 0.1%, 0.5%, 1%, 5%, 10%, values therebetween, etc.) in measurement of a biophysical parameter for a sample in different conditions. The improved reproducibility, repeatability, and/or reliability can be achieved, for example, by adjusting the biophysical parameter, images, score, metrics, and/or any suitable dataset or analysis thereof based on measured system and/or sample performance or other characteristics. However, the system and/or method can achieve any suitable reproducibility, repeatability, and/or reliability.

However, variants of the technology can confer any other suitable benefits and/or advantages.

As used herein, "substantially" or other words of approximation (e.g., "about," "approximately," etc.) can be within a predetermined error threshold or tolerance of a metric, component, or other reference (e.g., within 0.001%, 0.01%, 0.1%, 1%, 5%, 10%, 20%, 30%, etc. of a reference), or be otherwise interpreted.

3. System

The system 10 preferably functions to measure a dataset associated with a patient, analyze the patient dataset, determine a health status of a patient, adjust the dataset and/or analysis thereof, and/or can otherwise function. The dataset can include a set of images of a patient sample 15 (e.g., a plurality of images of each of a plurality of cells 17 of a patient sample; a plurality of images of each of a plurality of cells while the cells undergo deformation, stress, forces, pressure, etc.; etc.), a set of biophysical properties (e.g., mechanical properties, trajectory parameters, etc.) of the patient sample, system properties (e.g., applied force, pressure, tension, flow rate, vorticity, size, etc.), and/or any suitable data can be included. The patient sample can include leukocytes (e.g., a prepared sample as disclosed in U.S. patent application Ser. No. 17/575,388 titled 'SYSTEM AND METHOD FOR DETERMINING AN IMMUNE ACTIVATION STATE' filed 13 Jan. 2022 and/or U.S. patent application Ser. No. 17/575,422 titled 'SYSTEM AND METHOD FOR DETERMINING AN IMMUNE ACTIVATION STATE' filed 13 Jan. 2022, each of which is incorporated in its entirety by this reference, a sample consisting essentially of leukocytes from a patient, a blood sample from a patient, etc.), erythrocytes, thrombocytes, plasma, reticulocytes, platelets, cell debris, mechanical debris, dust, and/or any suitable sample associated with a patient (e.g., collected from a blood, stool, urine, biopsy, etc. sample). For instance, a sample can include between about 10,000 to 1,000,000 leukocytes 17 (and potentially red blood cells and/or red blood cell debris).

The sample 15 is preferably measured in (e.g., tested with, deformed in, using, etc.) a flow cytometer (e.g., deformability cytometer, constriction-based deformability cytometry (cDC), shear flow deformability cytometry (sDC), and/or extensional flow deformability cytometry (xDC), etc.). However, the sample can additionally or alternatively be measured using an atomic force microscope, using optical probes, and/or in any manner. For example, the sample can be loaded in a cartridge 100 (e.g., microfluidic cartridge, microfluidic cartridge, etc.) to be measured using flow cytometry. The cartridge can include any suitable microfluidic channels 150 or structures as disclosed in U.S. application Ser. No. 16/374,663 filed 3 Apr. 2019 and entitled 'SYSTEM AND METHOD FOR DEFORMING AND ANALYZING PARTICLES,' U.S. application Ser. No. 15/868,025 filed 11 Jan. 2018 entitled 'METHOD AND DEVICE FOR HIGH THROUGHPUT CELL DEFORMABILITY MEASUREMENTS,' U.S. application Ser. No. 16/676,352 filed 6 Nov. 2019 entitled 'METHOD AND DEVICE FOR HIGH-THROUGHPUT SOLUTION EXCHANGE FOR CELL AND PARTICLE SUSPENSIONS,' U.S. Pat. No. 9,464,977 filed 18 Oct. 2013 entitled 'SYSTEM AND METHOD FOR DEFORMING, IMAGING AND ANALYZING PARTICLES,' U.S. Pat. No. 10,252,260 filed 3 Apr. 2017 entitled 'SYSTEM AND METHOD FOR DEFORMING PARTICLES,' each of which is incorporated in its entirety by this reference, and/or any suitable cartridge can be used.

The cartridge preferably has a single z-plane that the particles flow in. However, the cartridge can have more than one z-plane (e.g., depending on the flow channel, flow rate, temperature, Reynolds number, etc.).

The particle velocity is preferably approximately 4 m/s (e.g., 1-6 m/s, 2-4 m/s, 3-5 m/s, 3-4.5 m/s, 1-4 m/s, 3 m/s, 3.5-4.5 m/s, 3.6 m/s, 3.7 m/s, 3.8 m/s, 3.9 m/s, 4 m/s, 4.1 m/s, 4.2 m/s, 4.3 m/s, 4.4 m/s, 5 m/s, values or ranges therebetween, etc.), but can be less than about 1 m/s and/or greater than about 6 m/s. In some variations, the result (e.g., biophysical parameter, index, health status, etc.) accuracy and/or reliability can depend on the particle velocity. For instance, when the flow rate is not approximately 4 m/s, the results can be difficult to adjust, inaccurate, require nonlinear adjustment, have chaotic adjustment, require larger adjustment and/or otherwise can have lower reliability and/or accuracy (e.g., relative to instances with particle velocity approximately 4 m/s), but may still be used (e.g., to determine a health status with a lower accuracy, reliability, reproducibility, etc.). However, the reliability can be independent of particle velocity (e.g., different models can be trained, used, etc. to ensure accuracy, reliability, etc. with different particle velocity), and/or the accuracy and/or reliability can otherwise depend on the particle velocity.

The microfluidic device can include and/or be coupled to a flow device, which functions to generate a fluid flow within the microfluidic device. The flow device can include a pump, an impeller, and/or any other flow device. The flow device can provide a negative and/or positive pressure (e.g., push fluid through, pull fluid through, etc. the microfluidic channel).

The detection system is preferably an image acquisition system 200 such as a microscope (e.g., an inverted microscope, an upright microscope, etc. such as configured to acquire bright-field images, dark-field images, fluorescent images, etc. of the sample), a camera, and/or any image acquisition system. Images are preferably acquired at a frame rate that is at least 10,000 frames per second such as 20,000; 50,000; 100,000; 200,000; 300,000; 500,000; 750,000; 1,000,000; 2,000,000; 5,000,000; 10,000,000 frames per second, etc. However, images can be acquired at less than 10,000 frames per second and/or at any rate. The field of view 250 of the image acquisition system is preferably centered proximal a stagnation point (e.g., a point where the flow paths and/or forces are balanced) of the deformation region. However, the stagnation point can be aligned to an edge, a corner, arbitrarily, a predetermined location, randomly, and/or otherwise aligned relative to the image acquisition system (e.g., within the captured images). However, the image acquisition system can be otherwise arranged.

The computing system 300 can function to process (e.g., analyze) the dataset, control a system operation (e.g., trigger data acquisition, time data acquisition, modify flow rate, etc.), determine a biophysical parameter, determine a health score, adjust a biophysical parameter (and/or health score, index, metric, etc.), determine a patient health status, and/or can otherwise function. The computing system can be local (e.g., a dedicated computer collocated with the data acquisition system), remote (e.g., cloud computer, server, database, etc.), and/or distributed in any manner. The computing system can include one or more: processors, microprocessors, computer processing units, graphics processing units, and/or any suitable processors. In a specific example, the computing system can include a GPU accelerated computation, which can be beneficial for rapidly and/or efficiently handling (e.g., processing) large datasets (such as generated by image sets).

The computing system can include one or more: image analyzer 320, filter 340, adjuster 360, index calculator, health scorer 380, and/or any suitable components or modules. The modules can be performed using different or the same executables (e.g., programs), on the same or different processor(s), and/or can otherwise be performed or operate in any manner.

The image analyzer 320 preferably functions to analyze a set of images. For example, the image analyzer can function to identify features in images, to process images (e.g., apply one or more image correction, warp images, etc.), and/or can otherwise function. The image analyzer can include a machine learning algorithm (e.g., K-means clustering, mean-shift clustering, Density-Based Spatial Clustering of Applications with Noise, Expectation-Maximization (EM) Clustering using Gaussian Mixture Model, Agglomerative Hierarchical Clustering, etc.), neural network (e.g., convolutional neural network, recurrent neural network, deep neural network, etc.), ray tracer, classifier 323 (e.g., binary classifier), and/or any suitable equations and/or algorithms can be used. The image analyzer can include edge detectors, object detectors, and/or any suitable detectors.

In some variants, the image analyzer can classify objects in the sample. For instance, leukocytes can be classified into (e.g., a class, a probability that a particle is in a class, etc.) a specific leukocyte subpopulation (e.g., monocyte, lymphocyte, neutrophil, basophil, eosinophil, etc.). In another example, the particles can be classified as (e.g., members of a class, probability that a particle is in a class, etc.) leukocytes or not leukocytes. However, the objects can additionally or alternatively be classified as erythrocytes, reticulocytes, platelets, cell debris, mechanical debris, dust, and/or in another suitable classification. The objects can be classified for each image, for each event (e.g., plurality of images of a given particle or object), for a population (e.g., when the sample is sorted into a given subpopulation of cells preferably with at least a threshold confidence of sorting), and/or can otherwise be classified.

The image analyzer can include an occlusion detector 327 which can function to determine when two (or more) particles are touching and/or collocated within an image and/or event. For example, the occlusion detector can detect occlusions based on particle size, particle dynamics, light intensity, image blur, based on a state history (e.g., a particle trajectory, change between frames, etc.), and/or in any manner.

The image analyzer can include a parameter extractor, which preferably functions to determine biophysical parameters from the dataset (e.g., image set, analyzed images, etc.). The parameter extractor can use equations, look-up tables, neural network (e.g., convolutional neural network, recurrent neural network, deep neural network, etc.), machine learning, and/or any suitable algorithms to determine the biophysical parameters. The biophysical parameters can include frame parameters (e.g., parameters extracted from, associated with, etc. a single image), event parameters (e.g., parameters extracted from, associated with, etc. a plurality of images of a common particle), population parameters (e.g., parameters extracted from images of a plurality of particles, distributions of frame parameters and/or event parameters for a plurality of particles, etc.), and/or any suitable parameters.

Exemplary biophysical parameters can include: structural parameters, trajectory parameters, patient parameters, location parameters (e.g., cell position relative to the image frame, relative to the channel, relative to the outlet, relative to the inlet, relative to the stagnation point, etc.), and/or any parameters. Examples of structural parameters include: shape (e.g., ellipticity, helicity, oblongness, circularity, curvature, skewness, etc.), aspect ratio (e.g., ratio of longest dimension to shortest dimension, ratio of length to width, etc.), size (e.g., lateral extent, longitudinal extent, depth, height, width, length, volume, surface area, etc.), constituent structure (e.g., cell membrane location, cell shape, cell wall structure, etc.), constituent morphology (e.g., cell morphology, cell shape, particle shape, etc.), internal structure (e.g., shape, morphology, size, etc. of a nucleus and/or other organelle of a cell), and/or any other structural parameters. Examples of patient parameters include: complete particle count, complete blood count, complete leukocyte count, complete neutrophil count, complete monocyte count, complete lymphocyte count, complete basophil count, complete eosinophil count, complete erythrocyte count, complete platelet count, constituent numerosity (e.g., number of cells and/or segments of cells, number of particles and/or segments of particles, etc.), presenting symptoms (e.g., patient temperature, blood pressure, weight, blood oxygenation, etc.), cell density, cell culture results, hydration, and/or any other sample parameters.

Figure 9:
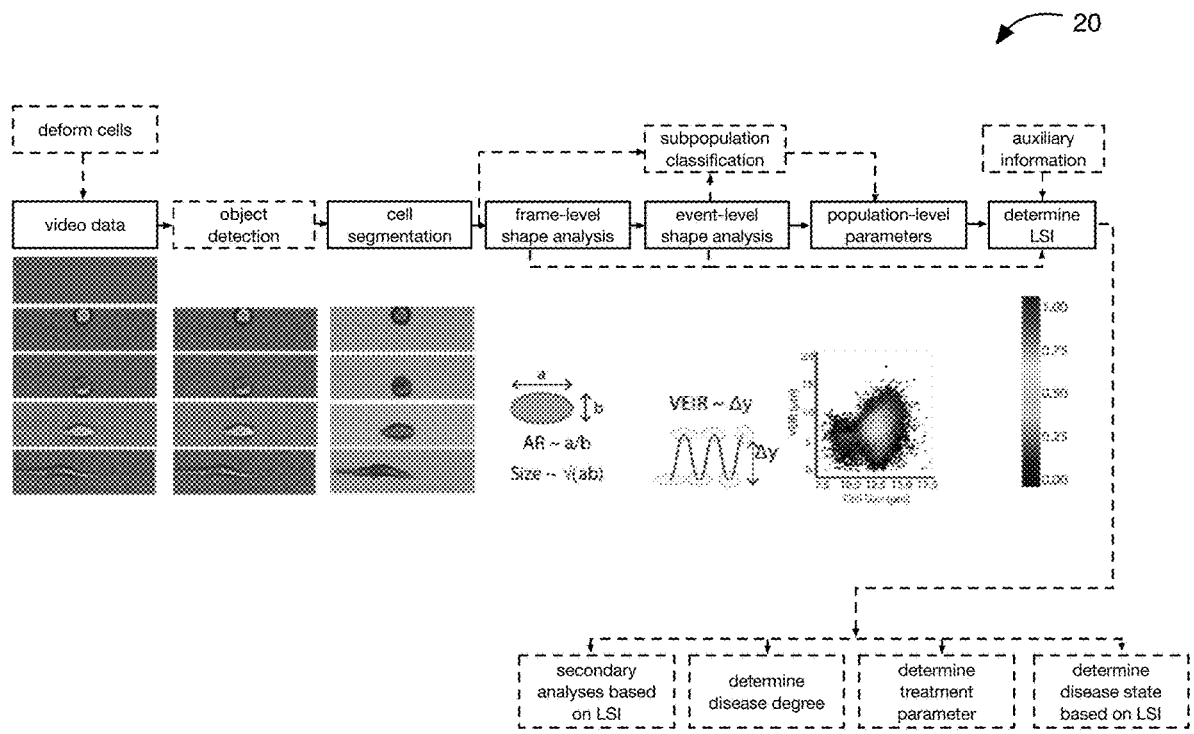
FIG. 9 is a schematic representation of an example of determining a patient health status based on a dataset.

Trajectory parameters can be parameters that are associated with and/or determined from the trajectory of the cell through the microfluidic cartridge (e.g., the deformation region of the microfluidic cartridge, the focusing region, etc.). The trajectory can be a series of discrete positions (e.g., of the centroid, of the center of mass, of a reference point, average position of the cell, etc.) of the cell, a continuous path of the cell, and/or correspond to any motion of the cells as they pass through the fluid flow (e.g., deformation region of the microfluidic cartridge). Examples of trajectory parameters include: direction of object and/or feature motion, speed of object and/or feature motion (e.g., average speed, instantaneous speed, etc.), acceleration of object and/or feature motion, an oscillation in the object and/or feature motion (e.g., an amplitude of the oscillation, a frequency of the oscillation, a phase of the oscillation, a modulation in the oscillation, a decay of the oscillation, as shown for example in FIG. 9, etc.), visco-elastic inertial response (VEIR), a deviation in the particle flow trajectory (e.g., from a linear path, an expected path, etc.), and/or any other trajectory parameters. The trajectory parameters can be determined based on a difference, sum, amplitude, maximum, minimum, average value of, and/or other characteristic of one or more positions of the trajectory. In variations where the trajectory parameters include an oscillation, the oscillation can correspond to an oscillation of a reference point (e.g., centroid, extrema, medoid, etc.), a reference axis (e.g., one or more dimension such as length, width, depth), one or more reference surface (e.g., object boundary, interior boundary of the object such as corresponding to an organelle boundary, etc.), reference volume (e.g., object volume, internal structure of the object, etc.), and/or other portion of the object. The oscillation preferably occurs along a reference axis perpendicular to the direction of motion of the object. However, the reference axis can be parallel to the direction of motion and/or have any orientation relative to the direction of motion. The oscillation amplitude is preferably on the micron-size scale (e.g., 1-10 µm, 10-100 µm, etc.), but can additionally or alternatively be nanometer scale (e.g., 1-100 nm, 100 nm-1 µm, etc.) and/or be any suitable distance.

The adjuster 360 functions to adjust a metric (e.g., a score, an index, a biophysical parameter, etc.). The metric is preferably adjusted based on a system property and/or a particle property, but can be adjusted based on an image property, an event property, a population property, and/or based on any suitable information. Exemplary system properties include: flow rate, temperature (average temperature, instantaneous temperature, etc.), temperature variance (e.g., throughout measurement, specified variance, etc.), flow rate variance (e.g., throughout measurement, specified variance, etc.), pressure, pressure variance (e.g., throughout measurement, specified variance, etc.), humidity, channel size, and/or any suitable system properties. Exemplary particle properties can include handedness (e.g., direction of fluid flow rotation, direction of particle propagation, etc.), particle population (e.g., leukocyte subpopulation), particle size, particle geometry, particle trajectory, particle acceleration, particle plane, and/or any suitable particle property(s). However, the metric can be adjusted in any manner.

Figure 4:
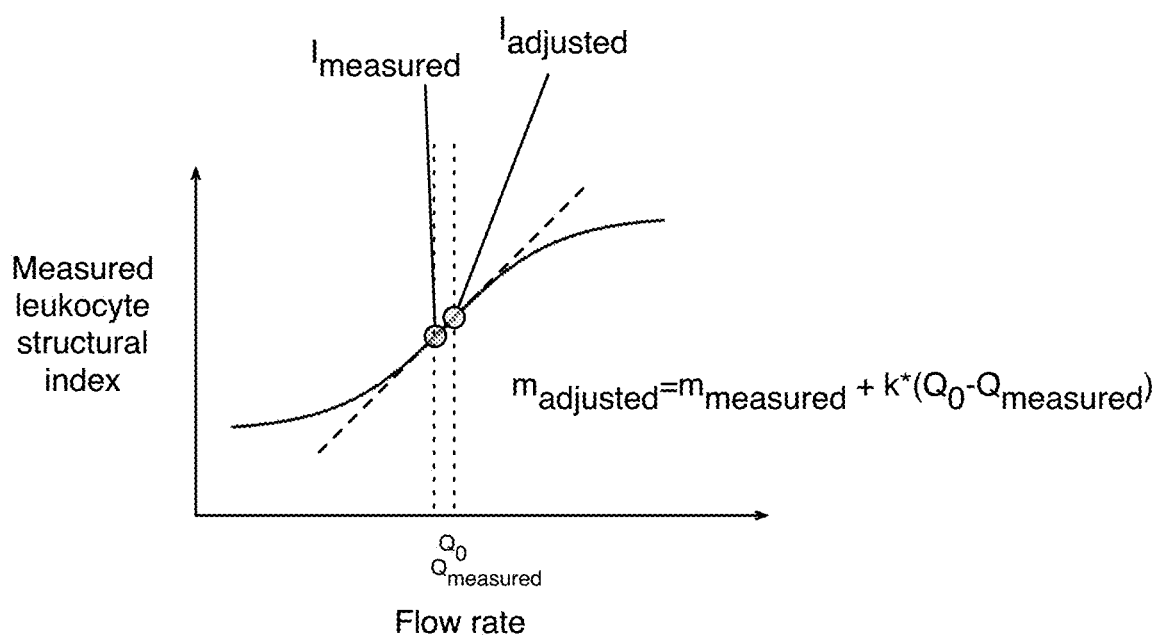
FIG. 4 is a schematic representation of an example of adjusting a measurement based on a flow rate.
Figure 6:
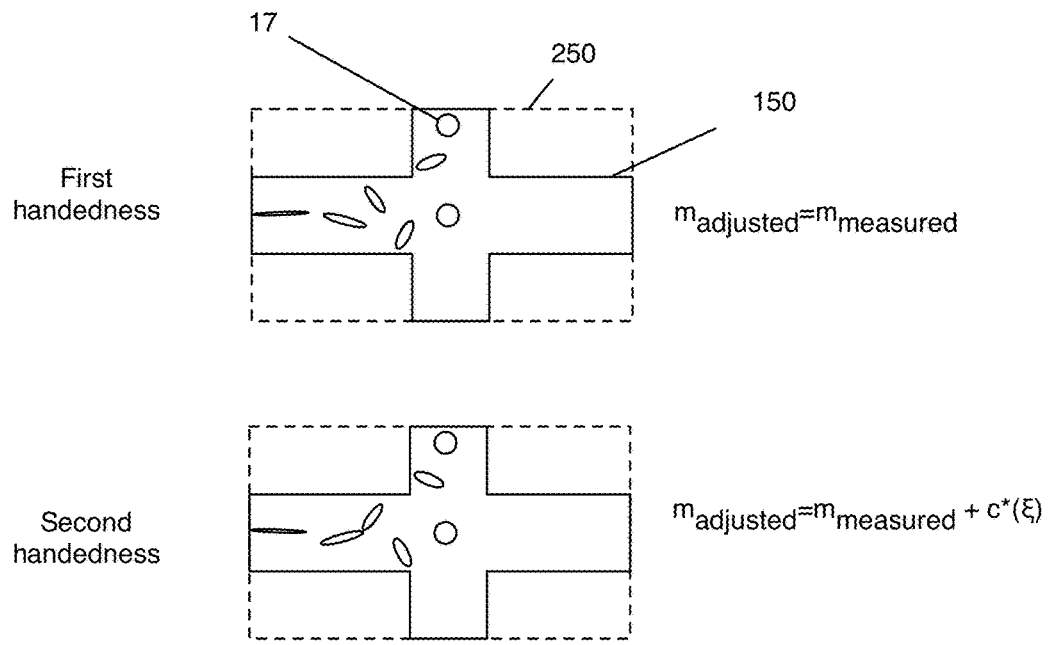
FIG. 6 is a schematic representation of examples of overlapping frames of particles with different handedness passing through the microfluidic channel, where a measurement can be adjusted based on a handedness of the flow path.
Figure 8:
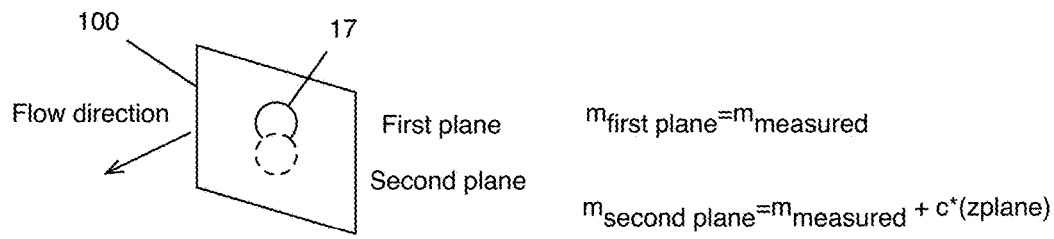
FIG. 8 is a schematic representation of exemplary z-planes a particle can be in, where an adjustment to a measurement can depend on the z-plane.

The adjuster preferably applies a linear adjustment, but can apply a nonlinear adjustment (e.g., quadratic, cubic, quartic, exponential, logarithmic, super exponential, sinusoidal, hyperbolic, hyperbolic trigonometric, inverse trigonometric, inverse polynomial, etc.) and/or any suitable adjustment. In a first specific example (as shown for instance in FIG. 4), an adjustment can be $m_{adjusted} = m_{determined} + k^*(Q_0 - Q_{measured})$, where $m_{adjusted}$ can be an adjusted metric, $m_{determined}$ can be a determined (e.g., measured) metric, k can be a constant (e.g., which can be determined empirically, measured, derived, physical constant, relationship, unit conversion, etc.), $Q_0$ can be a reference property value (for instance a reference flow rate; such as a target value, average value, mean value, modal value, median value, set value, expansion value such as for a Taylor expansion, etc.), and $Q_{measured}$ can be a measured property value. In a second specific example (as shown for instance in FIG. 6), an adjustment can be $m_{adjusted} = m_{determined} + c^*(\xi)$, where c can be a constant (e.g., which can be determined empirically, measured, derived, physical constant, relationship, unit conversion, etc.), and can be a handedness of the fluid flow (e.g., handedness of a particle trajectory). In a third illustrative example (as shown for instance in FIG. 8), an adjustment can be $m_{adjusted}=m_{determined}+m^*(zplane)$, where m can be a constant (e.g., which can be determined empirically, measured, derived, physical constant, relationship, unit conversion, etc.), and zplane can be a zplane of a particle (e.g., absolute z height within a channel, z height relative to a reference of the channel, z height relative to a second z plane of the channel, etc.). In a fourth specific example, an adjustment can include: $m_{adjusted}=m_{determined}+k^*(Q_0-Q_{measured})+c^*(\xi)+m^*(zplane)$. However, any suitable adjustment can be applied.

The adjuster is preferably only used when system properties are within a threshold range of a set value (e.g., average value, target value, set point, etc.). However, the adjuster can be used when the system properties are outside of the threshold range of a set value. This can be beneficial for ensuring that the parameters are in a linear regime and can be corrected using a linear correction (which is often more reliable, more reproducible, less contaminated by cross correlations with other parameters, and/or can otherwise be desirable or confer a technical advantage). The threshold range can be symmetric and/or asymmetric. The threshold range can be absolute values, relative values, and/or any suitable values. For example, the threshold range can be ±0.1%, ±0.5%, ±1%, ±2%, ±5%, ±10%, values or ranges therebetween, and/or any suitable range of values about a target value. In an illustrative example, the adjuster can be used when the system flow rate is within (above and/or below) 4% of a target flow rate.

When the system properties are outside the threshold range, the data is typically rejected (e.g., another sample is collected, measured, analyzed, etc.). However, the data can additionally or alternatively be adjusted (e.g., using a nonlinear adjustment, using the linear adjustment, etc.), be flagged (e.g., for potential inaccuracy), be used without adjustment, and/or can otherwise be processed and/or used.

In an illustrative example, the adjuster can adjust metrics associated with neutrophils. In a second illustrative example, the adjuster can adjust metrics associated with neutrophils with a particular handedness. In a third illustrative example, the adjuster can adjust metrics associated with neutrophils with a particular handedness in one manner and can adjust metrics associated with neutrophils with the other handedness in a different manner. In a fourth illustrative example, can adjust metrics associated with neutrophils with a particular handedness in one manner and can adjust metrics associated with monocytes in a different manner. However, the adjuster can adjust the metrics in any manner.

The index calculator preferably functions to determine an index from the biophysical properties. Each particle (e.g., each particle or object to be included in the health score determination) can also be associated with an index (e.g., an event index). However, the index can be a global index (e.g., single index associated with the patient), a subpopulation index, an image index, and/or any suitable index. The index calculator can include a machine learning algorithm, a neural network, an equation, a look-up table, a heuristic, and/or any suitable algorithm(s) can be used. In an illustrative example, the index calculator can ingest a particle size, particle trajectory parameter, cell count, a cell count for a single-cell or a leukocyte populations, and/or any suitable inputs can be used to determine the index.

The health scorer preferably functions to determine a health status of the patient. The health scorer 380 can be the same as and/or different from the index calculator. The health scorer can include a machine learning algorithm, a neural network, an equation, a look-up table, a heuristic, and/or any suitable algorithm(s) can be used. The health status is preferably determined based on the index, but can additionally or alternatively be determined based on the biophysical properties, images, dataset, and/or any suitable information. In some variations, auxiliary information (such as presenting symptoms, patient parameters, gender, race, age, height, weight, body mass index, time of day, recent travel, recent exposures, etc.) can be used (in addition to and/or alternative to the index) to determine the health status of the patient. The health status can be a diagnosis, a probability of a diagnosis, a scaled value (e.g., severity of a status, degree of activation, etc.), and/or any suitable value. For example, the health status can be indicative of an immune activation state of a patient and/or a degree of immune activation (e.g., cancer; metastatic cancer; sepsis; COVID-19 infection; sepsis-related condition; anemia; bleeding conditions; systemic inflammatory response syndrome; blood cell health; organ health; inflammation; cytokine release; cytokine storms; autoimmune disorders such as rheumatic disorders such as arthritis, lupus, etc.; graft-versus-host disease; etc.). In some variations, the health status can indicate a cause for the health status (e.g., bacterial, fungal, viral, chemical, etc.), and/or any suitable information.

4. Method

The method preferably functions to determine a health state of a patient, but can additionally or alternatively function to determine a biophysical parameter (and/or biophysical parameter distribution) of a patient, and/or perform any suitable function. The method can include: receiving a dataset S100; optionally, filtering the dataset S200; determining a metric S300; optionally, adjusting the metric S400; determining a health state of a patient S500; optionally, provisioning an intervention to the patient S600; and/or any suitable steps. The method can be performed using a system as described above, as system as disclosed in U.S. patent application Ser. No. 17/575,388 titled 'SYSTEM AND METHOD FOR DETERMINING AN IMMUNE ACTIVATION STATE' filed 13 Jan. 2022 and/or U.S. patent application Ser. No. 17/575,422 titled 'SYSTEM AND METHOD FOR DETERMINING AN IMMUNE ACTIVATION STATE' filed 13 Jan. 2022, each of which is incorporated in its entirety by this reference, and/or using any suitable system.

The method (and/or steps thereof) can be performed in parallel (e.g., concurrently, contemporaneously, simultaneously, etc.) and/or series (e.g., sequentially) for different samples (e.g., samples associated with different patients). Steps of the method can be performed contemporaneously (e.g., simultaneously, concurrently, etc.). For example, images associated with one event can be processed while another event is being measured (e.g., S200-S400 can be performed for a cell while a second cell is being measured). However, the steps of the method can be performed sequentially and/or in any suitable order or manner.

Receiving the dataset S100 functions to receive a dataset associated with a patient. The dataset can be received from a cytometer (e.g., flow cytometer, deformability cytometer, etc.), image acquisition system (e.g., camera), computing system (e.g., memory, database, storage, etc.), and/or from any suitable data source. The dataset is preferably a plurality of images of a blood sample of the patient (e.g., a plurality of images of each cell of a blood sample of the patient), but can additionally or alternatively include electrical data (e.g., resistance, conductivity, etc.), thermal data, probe measurements (e.g., a probe in contact with the sample, a probe in contact with the microfluidic channel(s), a probe in contact with the sheath fluid, etc.), pressure measurements, force measurements, and/or any suitable data.

Figure 7A:
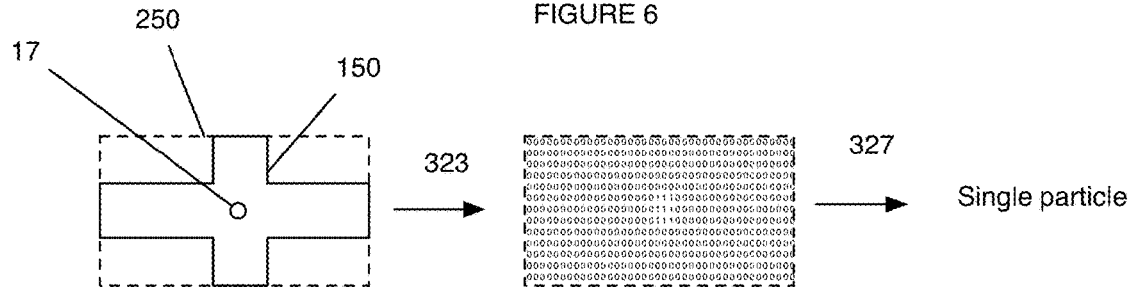
FIGS. 7A and 7B are schematic representations of examples of feature detectors for identifying overlapping particles.

Receiving the dataset can include processing the dataset. The dataset can be processed in real- or near-real time (e.g., as the dataset is acquired), delayed (e.g., until the entire dataset is acquired, until a target time for processing, etc.), and/or processed with any suitable timing. Processing the dataset can include: segmenting the dataset (e.g., into events, into a set of frames associated with a shared particle, into discrete time series, etc.), classifying the dataset (e.g., using a binary classifier, using a multi-class classifier, into particle or not particle, as shown for example in FIG. 7A, into a specific particle population, etc.), transforming an image (e.g., warping, scaling, translating, rotating, etc.; color balancing; etc.), and/or can otherwise process the dataset or portions thereof. In some variations, a processed dataset can be received (e.g., when processed data is stored and retrieved for later analysis).

As an illustrative example, a dataset can be segmented into events where each event can include a time series of frames (e.g., images) that include a common particle. Two or more events can share images (e.g., an image can include two or more particles). However, images can be unique to an event, and/or events and images can otherwise be related or associated with one another. The images can be segmented based on time (e.g., a predetermined number of frames, frames acquired within a predetermined amount of time, etc. of a first frame including a particle can be included in a segment), using a neural network, using machine learning, manually, and/or can otherwise be segmented.

In another illustrative example, events of a dataset (or particles thereof) can be classified into a particle subpopulation. For instance, particles can be classified into leukocytes, leukocyte subpopulations, erythrocytes, reticulocytes, platelets, cell debris, mechanical debris, dust, and/or any suitable classification(s), where the event can be processed (e.g., analyzed, adjusted, etc.) based on the classification. The events can be classified using a neural network, machine learning, based on image properties (e.g., features detected, number of features, feature shapes, light detected, etc.), and/or in any manner. As a specific example, a particle can be classified into a subpopulation based on a cell size, an optical intensity, organelle size, number of visible organelles (e.g., number of nuclei), and/or any suitable information.

Filtering the dataset S200 preferably functions to select data (e.g., high quality data, data with sufficient quality, data that meets one or more criteria, etc.) from the dataset (e.g., processed dataset, acquired dataset, raw dataset, measured dataset, etc.) to analyze. The dataset can be filtered before, during, and/or after the dataset has been received. The dataset is preferably filtered using a computing system (e.g., a filter thereof), but can be filtered using a filter of the measurement module (e.g., cytometer) and/or using any suitable component. The dataset can be filtered based on: measurement system properties (e.g., flow rate, temperature, humidity, pressure, etc.), patient sample properties (e.g., cell size, cell shape, cell count, biophysical properties, auxiliary data, etc.), image properties (e.g., brightness, contrast, occlusions, z-plane, type(s) of particles, etc.), event properties (e.g., particle trajectory, particle entrance position 252, particle entrance velocity, particle exit position 258, particle exit velocity, particle exit direction, particle rotation, etc.), population properties, and/or based on any suitable properties. The data (and/or dataset) can be filtered before, during (e.g., data associated with a first cell can be filtered while data for a second cell is being received), and/or after receiving the dataset.

The filtered dataset preferably includes data from between about 10,000 to 100,000 particles (e.g., cells of a patient), but can include data for fewer than 10,000 particles and/or greater than 100,000 particles. For each particle, the data preferably includes at least 10 frames (e.g., images, consecutive frames, etc.) that include the particle, which can provide a technical advantage particularly when determining a trajectory parameter for the particle. However, fewer than 10 frames can be sufficient (e.g., for particle counting, for particle morphological analysis, etc.). The set of frames associated with (e.g., that include) a particle can be referred to (e.g., in the collective) as an event and/or can be referenced in any manner.

The dataset (and/or data therein) can be filtered using a tree filter, a combination filter (e.g., filtering based on a filter score for the data for different filters), a cut-off filter (e.g., high pass, low pass, bandpass, bandstop, notch, etc.), Bloom filter, and/or any suitable filter structure(s) can be used.

The dataset can be filtered at a population level (e.g., to reject and/or accept the dataset for analysis), at an event level (e.g., to reject and/or admit an event in the filtered dataset), at a frame level (e.g., to reject and/or admit a frame into an event, to reject and/or admit a frame into the dataset, etc.), and/or can be filtered at any suitable level.

Typically, when data and/or the dataset does not meet a threshold value (e.g., the filter value), the data (and/or dataset) is excluded from the filtered dataset (e.g., is not analyzed). However, the data can additionally or alternatively be flagged (e.g., for having a value outside the threshold value), be adjusted (e.g., scaled, transformed, etc. such as to meet the threshold value), and/or can otherwise be manipulated and/or modified.

Examples of population level filtering (e.g., population level thresholds) can include: particle size distributions (e.g., distribution shape, distribution variance, etc.), system properties (e.g., flow rate, temperature, humidity, pressure, atmospheric pressure, etc.), particle subpopulation distributions (e.g., relative numbers of different leukocyte subpopulations, number of leukocyte subpopulations identified, confidence in leukocyte identification, etc.), and/or any suitable population level filters can be applied.

Examples of event level filters (e.g., event level thresholds) can include: occlusion filters, particle velocity filters, particle time filters (e.g., amount of time a particle spends in a deformation region), particle trajectory filters, particle entry filters, particle exit filters, particle z-plane, particle subpopulation, and/or any suitable filters.

Examples of frame level filters (e.g., frame level thresholds) can include: occlusion filters, blur filters, particle number filters (e.g., number of particles present in a frame), color filters, brightness filters, contrast filters, focal plane filters (e.g., sharpness filters), and/or any suitable filters.

Figure 5A:
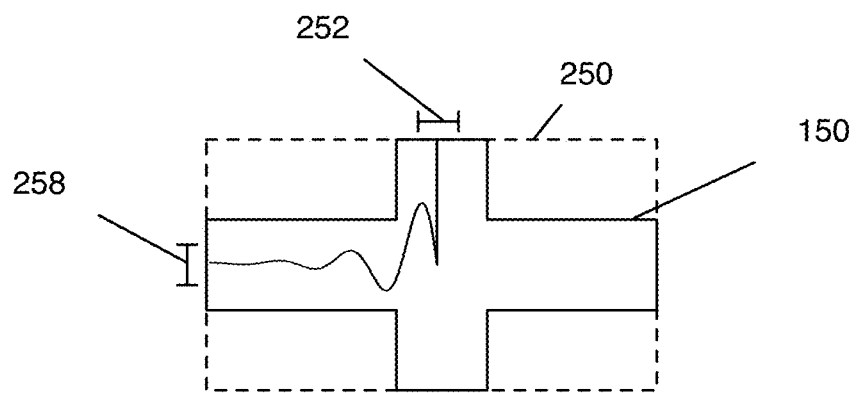
FIGS. 5A-5C are schematic representations of examples of events that pass (5A) or fail (5B or 5C) an event filter based on an entrance and/or exit position of a particle within the microfluidic channel.
Figure 5B:
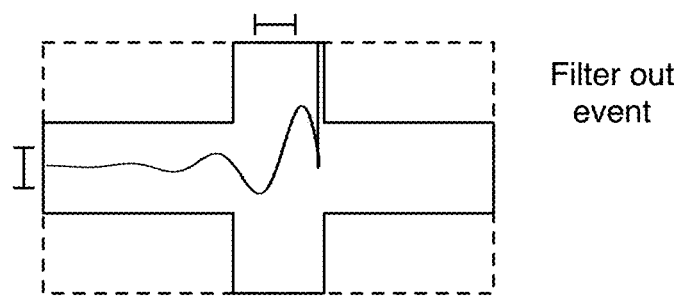
Figure 5C:
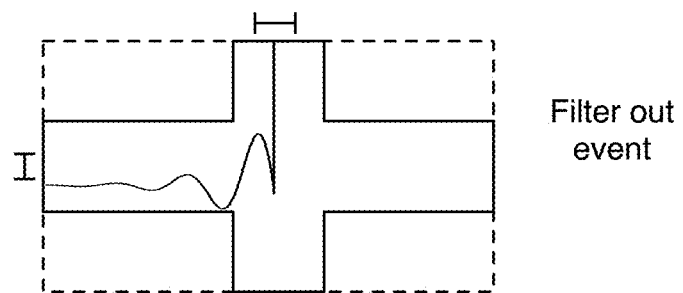

In a first specific example (as shown for instance in FIG. 5A, FIG. 5B, and/or FIG. 5C), the filtered dataset can include data (e.g., events) associated with particles that enter and/or exit a region of interest of the image within a threshold window (e.g., at least a threshold distance from a channel edge, proximal a center of the channel, in a region between approximately 25-75% of the channel opening or exit, within a threshold pixel window of an image field-of-view, etc.) and can exclude data associated with particles that enter and/or exit the region of interest outside of the threshold window.

Figure 7B:

In a second specific example (as shown for instance in FIG. 7A and/or FIG. 7B), the filtered dataset can include data (e.g., events, images, etc.) associated with particles in isolation (e.g., that are not obscured, contacting, etc. other particles) and can exclude data associated with particles that are obscured. The obscured particles can be identified based on a particle size (e.g., particularly but not exclusively before the particle has been deformed), based on a particle number, based on a change in particle position between frames, based on an intensity of an image (e.g., contrast of the particle compared to an anticipated contrast), and/or in any manner. In variations of the second specific example, frames and/or events that include 2 or more particles can be included in the filtered dataset, particularly but not exclusively when the 2 or more particles are isolated from each other, are only present in a subset of images, have a threshold distance between the particles, have a threshold timing difference between the particles (e.g., threshold time difference between the particle entrances), and/or can otherwise be included and/or excluded from the filtered dataset.

In a third specific, an event can be filtered based on a z-plane that the particle is traversing the channel through. For instance, particles that are detected in a z-plane of the channel can be included in the filtered dataset and particles that are detected in a different z-plane can be excluded from the filtered dataset. The included z-plane can be a preferred z-plane, a z-plane in the focal plane of an image acquisition system, a first z-plane (e.g., a z-plane that a first measured particle is in, a z-plane selected from a previous sample, etc.), a z-plane at least a predetermined distance from a channel wall (e.g., bottom, top, etc.), and/or any suitable z-plane can be selected.

In a fourth specific example, an event can be filtered based on a number of consecutive frames associated with the event. For instance, when more than 10 frames are associated with a particle, the data can be included in the filtered dataset and/or when less than 10 frames are associated with a particle the data can be excluded from the filtered dataset.

In a fifth specific example, a dataset can be filtered based on a flow rate in a cartridge. For instance, when the flow rate is within a threshold of a target flow rate (e.g., within about ±0.5%, 1%, 2%, 5%, 10%, 20%, values or ranges therebetween, etc.), the data can be included in the dataset.

In a sixth specific example, a dataset can be filtered based on a temperature of the sample during measurement. For instance, when the temperature is within a threshold of a target temperature (e.g., within about ±0.5%, 1%, 2%, 5%, 10%, 20%, values or ranges therebetween, etc.; within ±0.1°, ±0.5°, ±1°, ±2°, ±5°, ±10°, values or ranges therebetween, etc.; etc.), the data can be included in the dataset.

In a seventh specific example, any or all of the preceding first through sixth specific filtering examples can be combined and/or applied. Filter results can be combined by voting (e.g., voting to include or exclude data from the dataset), by a preference (e.g., ranked preference for filtering based on the filter results), absolute filtering (e.g., when data would be excluded by any filter, excluding the data from the dataset), a threshold number of filters can be used to include and/or exclude data (e.g., 1, 2, 3, 4, 5, 6, 10, etc. filters), and/or the filters can otherwise be combined.

However, the data and/or dataset can be filtered in any manner.

Determining a metric S300 functions to determine a metric (e.g., a biophysical parameter, etc.) associated with each particle in a dataset (e.g., processed dataset, filtered dataset, measured dataset, etc.). The metric(s) are preferably determined using a computing system (e.g., image analyzer, etc.), but can be determined using any suitable system and/or component. The metric can be used (directly used, indirectly used, etc.) to determine a health status of the patient. The metric can be a numerical value, a distribution, a category, a normalized value, a relative value, an absolute value, and/or be any suitable value. The metric is preferably determined after filtering a dataset, but can be determined before and/or during dataset filtering (e.g., a metric for a first cell can be determined while data for a second cell is being filtered).

The metric can be determined using a machine learning algorithm, a neural network, equations, heuristics, fits, an estimator (e.g., Monte Carlo simulation, Kalman filter, extended Kalman filter, etc.), and/or using any suitable algorithm(s) and/or methods.

Inputs used to determine the metric can include: a dataset (e.g., filtered dataset, processed dataset, received dataset, etc.), a subset of the dataset (e.g., event data, frame data, etc.), system data (e.g., cartridge geometry, cartridge size, channel size, channel shape, temperature, flow rate, pressure, etc.), auxiliary data (e.g., patient data, patient demographics, etc.), and/or any suitable information. The metrics (e.g., the outputs) can include biophysical properties (e.g., of a particle, of a sample, etc.), an index (e.g., a leukocyte structural index), and/or any suitable information. In some variations, one or more metrics can be used to determine other metrics.

Determining the metric can include determining one or more system properties S350. The system properties can be determined from the dataset (or subset thereof), from sensor data, and/or from any suitable data. In an illustrative example, a flow rate can be determined using a plurality of images of one or more particles within the channel (e.g., within the deformation region, within a focusing region, within a straight region, within a region that does not divert the particles, within a flow rate measurement region, etc. of the channel). In this example, the flow rate can be determined based on a frame rate (e.g., amount of time between acquired images), a particle displacement (e.g., distance a particle moves between images), a particle size (e.g., average particle size, expected particle size, etc.), a temperature, a Reynolds number, a channel aspect ratio, channel geometry, Dean number, channel hydraulic diameter, particle confinement ratio, and/or using any suitable information. In a variation of the illustrative example, determining the flow rate S355 can include: segmenting a plurality of images into a foreground (e.g., one or more cells or particles) and a background, determining a displacement of the foreground between images, and determining the flow rate based on the displacement (in addition to an image frame rate, particle size, channel size, etc.).

In some variations, the system properties can be corrected S370 after determining a metric (e.g., correcting the system properties based on the metric). As an illustrative example, the flow rate can be corrected based on a measured particle size distribution.

Determining the metrics can include aggregating the metrics which can function to summarize the metrics, determine sample level properties, and/or can otherwise function. The aggregated metrics can be referred to as a feature and/or referred to by any suitable name. The metrics can be aggregated at a sample level, at a sample subpopulation level, based on a shared property (e.g., aggregated based on a shared z-plane, shared handedness, etc.). In some variations, the metrics can be adjusted (e.g., as in S400) before metric aggregation. The metrics can be aggregated based on a particle subpopulation, one or more statistical descriptors, and/or based on any suitable information. Examples of statistical descriptors include: averages, $n^{th}$ percentile values (e.g., $0.1^{th}$, $1^{st}$, $5^{th}$, $10^{th}$, $20^{th}$, $25^{th}$, $50^{th}$, $75^{th}$, $80^{th}$, $90^{th}$, $95^{th}$, $99^{th}$, $99.9^{th}$, values therebetween, etc. percentile values), moments of a distribution (e.g., skewness, kurtosis, L-moments, etc.), dispersion (e.g., variance, standard deviation, coefficient of variation, range, interquartile ranges, etc.), modal values, median values, index of dispersion, and/or any suitable statistical descriptors. Some examples of aggregated metrics include: an average particle size (e.g., for neutrophils, monocyte, lymphocyte, neutrophil, basophil, eosinophil, combinations or subcombinations thereof, etc.), an average VEIR (e.g., for neutrophils, monocyte, lymphocyte, neutrophil, basophil, eosinophil, combinations or subcombinations thereof, etc.), a $75^{th}$ percentile VEIR (e.g., for neutrophils, monocyte, lymphocyte, neutrophil, basophil, eosinophil, combinations or subcombinations thereof, etc.), an average aspect ratio (e.g., for neutrophils, monocyte, lymphocyte, neutrophil, basophil, eosinophil, combinations or subcombinations thereof, etc.), an aspect ratio dispersion (e.g., for neutrophils, monocyte, lymphocyte, neutrophil, basophil, eosinophil, combinations or subcombinations thereof, etc.), a VEIR dispersion (e.g., for neutrophils, monocyte, lymphocyte, neutrophil, basophil, eosinophil, combinations or subcombinations thereof, etc.), and/or any suitable aggregated metrics can be determined. Each aggregated metric can be a scalar (e.g., single value), vector (e.g., set of values for each subpopulation, set of values of aggregated metrics, etc.), matrix (e.g., include correlations between aggregated metrics), tensor, and/or have any suitable form.

Adjusting a metric S400 preferably functions to correct, transform, normalize, and/or otherwise modify the metric. Adjusting the metric can provide a technical advantage of increasing a reproducibility, reliability, repeatability, and/or otherwise improve a determination of the metric and/or health status of the patient. The metrics are preferably adjusted using a computing system (e.g., adjuster, etc.), but can be determined using any suitable system and/or component. The metric can be adjusted before (e.g., a metric associated with a particle can be adjusted before a feature is determined), during (e.g., a metric associated with a first particle can be adjusted while a metric associated with a second particle is determined), and/or after S300. The adjusted metric can be a determined metric, an aggregated metric (e.g., feature), an index (e.g., a value derived from the metrics, aggregated metrics, etc. such as in S500), and/or any suitable metric.

The metric is preferably linearly adjusted, but can be adjusted nonlinearly. Metrics are preferably adjusted in the same manner, but can be adjusted in different manners. The adjustment (e.g., adjustment coefficient) can depend on a system property (e.g., flow rate, temperature, humidity, pressure, channel geometry, etc.), sample property (e.g., sample concentration, sample composition, etc.), particle property (e.g., particle size, particle metric, particle population, etc.), and/or any suitable information. The adjustment (e.g., adjustment coefficient) can be determined empirically, heuristically, physically, determined using machine learning, determined using a neural network, and/or can otherwise be determined. In a first specific example, an adjustment coefficient can depend on a particle subpopulation. For instance, a first adjustment can be used to adjust metrics associated with neutrophils and a second adjustment can be used to adjust metrics associated with monocytes. In a second specific example, which adjustments are applied can depend on a particle subpopulation. For instance, a z-plane adjustment can be applied to neutrophils (e.g., but not lymphocytes). However, all adjustments can be applied to all subpopulations, and/or any suitable adjustments can be applied to any suitable particles.

In a first specific example (as shown for instance in FIG. 4), an adjustment can be $m_{adjusted}=m_{determined}+k^*(Q_0-Q_{measured})$, where $m_{adjusted}$ can be an adjusted metric, $m_{determined}$ can be a determined (e.g., measured) metric, k can be a constant (e.g., which can be determined empirically, measured, derived, physical constant, relationship, unit conversion, etc.; adjustment coefficient; etc.), $Q_0$ can be a reference property value (for instance a reference flow rate; such as a target value, average value, mean value, modal value, median value, set value, expansion value such as for a Taylor expansion, etc.), and $Q_{measured}$ can be a measured property value. In a second specific example (as shown for instance in FIG. 6), an adjustment can be $m_{adjusted}=m_{determined}+c^*(\xi)$, where c can be a constant (e.g., which can be determined empirically, measured, derived, physical constant, relationship, unit conversion, etc.), and can be a handedness of a particle (e.g., handedness of a particle trajectory). In a third illustrative example (as shown for instance in FIG. 8), an adjustment can be $m_{adjusted}=m_{determined}+m^*(zplane)$, where m can be a constant (e.g., which can be determined empirically, measured, derived, physical constant, relationship, unit conversion, etc.), and zplane can be a zplane of a particle (e.g., absolute z height within a channel, z height relative to a reference of the channel, z height relative to a second z plane of the channel, etc.). In a fourth specific example, an adjustment can include: $m_{adjusted}=m_{determined}+k^*(Q_0-Q_{measured})+c^*(\xi)+m^*(zplane)$. However, any suitable adjustment can be applied.

In some variants, S400 can include adjusting a system property. For example, a system flow rate can be modified so that the measured flow rate matches a target flow rate (and thereby removes a need to adjust the flow rate). In another example, a temperature of the sample (and/or cartridge) can be modified to ensure that the sample is within a threshold range of a target temperature during measurement. The system property is preferably adjusted before measuring a dataset, but can be adjusted during the measurement.

Determining the health state S500 preferably functions to determine an immune activation and/or response of the patient. The health state is preferably determined using a computing system (e.g., index calculator, health scorer, etc.), but can be determined using any suitable system and/or component. The patient health state can include an index (e.g., leukocyte structural index, normalized index such as between 0-1, a nonnormalized index such as 0-10, 0-100, 0.1-10, 0.1-100, 1-10, 1-100, etc.), a diagnosis, a classification, a probability of a diagnosis applying to a patient, and/or any suitable information.

The health state can be determined from a model, an equation, a look-up table, a machine learning algorithm (e.g., trained to output a score, trained to output an index, trained to output a disease state, etc.), and/or can otherwise be determined. Examples of models that can be used include: logistic regressions (e.g., linear logistic regressions, nonlinear logistic regressions, etc.), decision trees, Bayesian classifiers, nearest neighbor techniques, support vector machines, decision forests (e.g., random forest), neural networks, gradient boosting, and/or any model can be used. The model can be: a predetermined model, a general model, a model selected based on the auxiliary information, and/or any other suitable model.

Inputs to the model can include: one or more metrics (e.g., determined metrics, adjusted metrics, aggregated metrics, features, adjusted aggregated metrics, adjusted features, etc.); one or more parameters; auxiliary information such as age, maturity (e.g., infant, toddler, child, adolescent, adult, etc.), weight, height, race, sex, temperature, body mass index, body fat ratio, preexisting conditions, duration of symptoms, onset of symptoms, travel, blood oxygenation levels, blood pressure, infection source, etc.; treatment parameters (e.g., hospital stay; administered treatments; etc.); collection parameters (e.g., temperature; other compounds found in the sample; etc.); images (e.g., from the set of images); images and/or analyses thereof of cells in different illumination conditions (e.g., different intensity light, different wavelength light, etc.); different event level information; frame-level analyses; population analyses; and/or any inputs. In an illustrative example, the inputs can include an aggregated trajectory parameter (e.g., average VEIR, $75^{th}$ percentile VEIR, average VEIR for monocytes, $75^{th}$ percentile VEIR for monocytes, etc.), a cell size (e.g., average cell size, average cell size for neutrophils, etc.), and/or a cell enumeration (e.g., number of neutrophils, number of leukocytes, etc.). The inputs are preferably determined based on a training dataset, but can be determined in any manner.

Outputs of the model can include: an index (e.g., a health state index; a leukocyte structural index (LSI); an IntelliSep Index (ISI); a value between 0-1, 0-10, etc.; a score; a number of constituents with a parameter and/or combination of parameters that exceeds a threshold such as the total number of constituents exceeding the threshold, a fraction of the total number of constituents exceeding the threshold, etc.; a probability; etc.), a health state, a health state severity, a probability of a health state, and/or any output.

In an illustrative example, the health state can be determined based on the index. When the index exceeds a threshold (e.g., 0.01, 0.05, 0.1, 0.2, 0.25, 0.3, 0.4, 0.5, 0.6, 0.7, 0.75, 0.8, 0.9, 0.95, 0.99, 1, etc.), the health state can indicate that a patient has (or is likely to have such as probability at least 50%) a condition. When the index is below a threshold (e.g., 0.01, 0.05, 0.1, 0.2, 0.25, 0.3, 0.4, 0.5, 0.6, 0.7, 0.75, 0.8, 0.9, 0.85, 0.99, 1, 2, 3, 4, 5, 6, 7, 8, 9, etc.), the health state can indicate that a patient does not have a condition (or is likely to not such as the probability that the patient does not have the condition is at least 50%). However, the index falling below a threshold can be indicative of a condition, the index exceeding a threshold can be indicative of not having a condition, and/or the index can be used in any manner. The threshold can be determined based on a training dataset (e.g., in a similar manner to how the model is generated, in a similar manner to how the inputs to the model are selected), be predetermined, be determined according to an equation (e.g., an equation based on and/or that accounts for the auxiliary sample information), and/or can be otherwise determined.

Provisioning an intervention S600 can function to provide an intervention to the patient. The intervention preferably depends on the health state (e.g., immune activation state), but can depend on the biophysical properties, patient data, and/or any suitable data and/or information. Provisioning an intervention is preferably performed automatically (e.g., a computing system generates a suggestion based on the health state), but can be performed manually and/or in any manner. Examples of interventions include: tracking the patient's disease state progression over time, determining a treatment parameter (e.g., estimated hospital stay duration, estimated triage requirements, etc.), initiating secondary analyses (e.g., innate immune activation assays such as light microscopy to assay structural features; cytology assays; chemical change assays such as using immunofluorescence labeling of CD11b, CD18, CD64, CD66b, flow cytometry, etc.; transcriptomic signatures analyses; etc.), suggesting an antibiotic regiment, suggesting an antiviral regiment, suggesting a chemotherapy regiment, informing a health care provider of a patient health state, indicating an urgency of a health state, informing a patient of a health state, displaying a health state, and/or other suitable interventions.

The methods of the preferred embodiment and variations thereof can be embodied and/or implemented at least in part as a machine configured to receive a computer-readable medium storing computer-readable instructions. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

Embodiments of the system and/or method can include every combination and permutation of the various system components and the various method processes, wherein one or more instances of the method and/or processes described herein can be performed asynchronously (e.g., sequentially), concurrently (e.g., in parallel), or in any other suitable order by and/or using one or more instances of the systems, elements, and/or entities described herein.

As a person skilled in the art will recognize from the previous detailed description and from the figures and claims, modifications and changes can be made to the preferred embodiments of the invention without departing from the scope of this invention defined in the following claims.

We claim:

1. A method for determining a sepsis condition of a subject comprising:
   receiving a dataset generated from a blood sample of the subject, wherein the dataset comprises, for each leukocyte of the blood sample, a plurality of images of the leukocyte as the leukocyte is deformed within a deformation region of a microfluidic channel;
   filtering the dataset to exclude images comprising overlapping leukocytes, comprising detecting the overlapping leukocytes based on a monotonicity in feature motion between images of the leukocyte;
   determining a biophysical parameter dataset by, for each leukocyte of the blood sample:
      determining one or more biophysical parameter associated with the respective leukocyte based on the plurality of images associated with the respective leukocyte;
      linearly adjusting the one or more biophysical parameters based on at least one of a flow rate and a path traversed by the respective leukocyte; and
   determining a numerical index based on the biophysical parameter dataset; and
   based on the numerical index, determining a probability that the subject is experiencing sepsis.

2. The method of claim 1, wherein filtering the dataset further comprises filtering the dataset by for each leukocyte of the blood sample:
   determining an entrance position of the respective leukocyte into the deformation region and an exit position of the leukocyte from the deformation region based on the plurality of images associated with the respective leukocyte; and excluding images associated with the respective leukocyte from the dataset when the entrance position is not within a threshold distance of an expected entrance position or the exit position is not within a threshold distance of an expected exit position.

3. The method of claim 1, further comprising, for each leukocyte of the blood sample, determining a cell type of the leukocyte, wherein linearly adjusting the one or more biophysical parameters further depends on the cell type.

4. The method of claim 1, wherein filtering the dataset further comprises filtering the dataset comprising, for each leukocyte of the blood sample:
   determining a cell type of the respective leukocyte; and
   including images associated with the respective leukocyte in the dataset depends on the cell type of the respective leukocyte.

5. The method of claim 3, wherein when the cell type of a leukocyte is a neutrophil, linearly adjusting the one or more biophysical parameters associated with the leukocyte further comprises adjusting the one or more biophysical parameters based on a z-plane of the leukocyte.

6. The method of claim 1, wherein adjusting the one or more biophysical parameters based on the flow path comprises linearly adjusting the one or more biophysical parameters when the path of the leukocyte comprises a first handedness and not linearly adjusting the one or more biophysical parameters when the path of the leukocyte comprises a second handedness.

7. The method of claim 1, wherein determining the numerical index comprises determining the numerical index based on an average size of neutrophils and a $75^{th}$ percentile of a viscoelastic inertial response of monocytes.

8. The method of claim 1, further comprising determining an average flow rate of leukocytes of the blood sample through the microfluidic channel, wherein when the average flow rate of the leukocytes through the microfluidic channel is less than 1 m/s or greater than 5 m/s, the probability is not determined.

9. The method of claim 1, wherein determining a biophysical parameter dataset further comprises, for each leukocyte of the blood sample:
   extracting features from the plurality of images associated with the respective leukocyte; and
   determining at least one of a trajectory of the respective leukocyte within the deformation region of the microfluidic channel or a structural parameter of the respective leukocyte based on the features.

10. The method of claim 9, wherein, for each leukocyte of the blood sample, determining a trajectory of the respective leukocyte comprises determining an amplitude of an oscillation of a centroid of the respective leukocyte within the deformation region of the microfluidic channel.

11. The method of claim 10, wherein, for each leukocyte of the blood sample, determining the amplitude of the oscillation of the centroid of the respective leukocyte comprises determining the amplitude of the oscillation of the centroid of the respective leukocyte in a direction orthogonal to a direction of motion of the leukocyte within the deformation region.

12. The method of claim 9, wherein, for each leukocyte of the blood sample, determining a structural parameter of the respective leukocyte comprises determining a cell size or a cell aspect ratio of the respective leukocyte.

13. The method of claim 1, wherein determining the numerical index based on the biophysical parameter dataset comprises determining the numerical index based on logistic regression analysis of the biophysical parameter dataset, wherein determining a probability that the subject is experiencing sepsis comprises comparing the numerical index to a threshold.

* * * * *